US010073008B2

(12) United States Patent
Weickert et al.

(10) Patent No.: US 10,073,008 B2
(45) Date of Patent: *Sep. 11, 2018

(54) ELECTROSTATIC SENSOR (71) Applicant: General Electric Company, Schenectady, NY (US)

(72) Inventors: John David Weickert, Fairfield, OH (US); Andrew Scott Kessie, Springboro, OH (US); Philip T. Smith, Cincinnati, OH (US); Charles Rickards, Cincinnati, OH (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/007,282

(22) Filed: Jan. 27, 2016

(65) Prior Publication Data

US 2017/0212011 A1 Jul. 27, 2017

(51) Int. Cl.
  *G01M 15/14* (2006.01)
  *G01N 15/06* (2006.01)
  (Continued)

(52) U.S. Cl.
  CPC ......... *G01M 15/14* (2013.01); *F01D 21/003* (2013.01); *G01N 15/0656* (2013.01);
  (Continued)

(58) Field of Classification Search
  USPC ...................................................... 73/112.01
  See application file for complete search history.

(56) References Cited

U.S. PATENT DOCUMENTS 3,917,432 A 11/1975 Feuerstein
4,249,131 A 2/1981 Owen
(Continued)

FOREIGN PATENT DOCUMENTS

GB 2335745 A 9/1999
GB 2482480 A 2/2012
(Continued)

OTHER PUBLICATIONS

U.S. Non-Final Office Action issued in Connection with Related U.S. Appl. No. 15/007,289 dated Apr. 14, 2017.
(Continued)

*Primary Examiner* — Eric S McCall
(74) *Attorney, Agent, or Firm* — General Electric Company; Pamela Kachur (57) ABSTRACT The present disclosure is directed to an integrated electrostatic sensor for detecting dust and/or other airborne particulates in an engine, e.g. in an aircraft gas turbine engine. The electrostatic sensor includes an outer housing having a sensing face, an electrode configured within the outer housing adjacent to the sensing face, and an amplifier configured with the electrode. The electrode contains a plurality of electrons configured to move as charged dust particles flow past the sensing face. Thus, the amplifier is configured to detect a dust level as a function of the electron movement. The electrostatic sensor also includes a circuit board configured within the outer housing and electrically coupled to the amplifier. Thus, the circuit board is configured to send the one or more signals to a controller of the engine indicative of the dust level.

15 Claims, 5 Drawing Sheets (51) Int. Cl.
*F01D 21/00* (2006.01)
*G01N 15/00* (2006.01)
*G01N 15/02* (2006.01)

(52) U.S. Cl.
CPC .... *F05D 2220/323* (2013.01); *F05D 2260/83* (2013.01); *G01N 15/0266* (2013.01); *G01N 2015/0046* (2013.01)

(56) References Cited

U.S. PATENT DOCUMENTS

| | | | |
|---|---|---|---|
| 4,531,402 A | | 7/1985 | Reif et al. |
| 4,531,486 A | | 7/1985 | Reif et al. |
| 4,888,948 A | | 12/1989 | Fisher |
| 5,070,722 A | * | 12/1991 | Hawman ............... G01N 29/14 73/28.01 |
| 5,602,543 A | | 2/1997 | Prata |
| 6,668,655 B2 | | 12/2003 | Harrold |
| 7,275,415 B2 | | 10/2007 | Rhodes |
| 7,419,532 B2 | | 9/2008 | Sellers |
| 7,518,098 B2 | | 4/2009 | Mack |
| 7,549,317 B2 | | 6/2009 | Rhodes |
| 7,628,007 B2 | | 12/2009 | Kittelson et al. |
| 7,895,818 B2 | | 3/2011 | Snell |
| 8,037,738 B2 | | 10/2011 | Boehler et al. |
| 8,256,277 B2 | | 9/2012 | Khibnik |
| 8,424,279 B2 | | 4/2013 | Rajamani |
| 8,459,103 B2 | | 6/2013 | Khibnik |
| 8,761,490 B2 | | 6/2014 | Scheid |
| 8,941,396 B2 | | 1/2015 | Cok |
| 9,010,198 B2 | | 4/2015 | Rajamani |
| 9,074,868 B2 | | 7/2015 | Bendall |
| 9,714,967 B1 | | 7/2017 | Weickert et al. |
| 2006/0156791 A1 | | 7/2006 | Tikkanen et al. |
| 2009/0045967 A1 | | 2/2009 | Bandholz |
| 2010/0287907 A1 | * | 11/2010 | Agrawal ............... F02C 7/052 60/39.091 |
| 2010/0288034 A1 | * | 11/2010 | Agrawal ............... F02C 7/052 73/112.01 |
| 2010/0292905 A1 | * | 11/2010 | Agrawal ............... F02C 9/00 701/100 |
| 2010/0313639 A1 | * | 12/2010 | Khibnik ................ F01D 17/24 73/112.01 |
| 2011/0062973 A1 | | 3/2011 | Paterson |
| 2011/0079015 A1 | * | 4/2011 | Geis ................... F01D 17/02 60/779 |
| 2011/0179763 A1 | * | 7/2011 | Rajamani ............. B01D 45/14 60/39.092 |
| 2011/0192211 A1 | | 8/2011 | Yokoi et al. |
| 2012/0068862 A1 | | 3/2012 | Tillotson |
| 2012/0324987 A1 | | 12/2012 | Khibnik |
| 2013/0025348 A1 | | 1/2013 | Rajamani |
| 2013/0058419 A1 | | 3/2013 | Ye |
| 2013/0180271 A1 | | 7/2013 | Kuczynski |
| 2013/0193978 A1 | | 8/2013 | Woolley |
| 2013/0220004 A1 | * | 8/2013 | Epstein ................ G01M 15/14 73/112.01 |
| 2014/0331743 A1 | | 11/2014 | Kwon |

FOREIGN PATENT DOCUMENTS

| | | |
|---|---|---|
| GB | 2842480 A | 2/2012 |
| GB | 2496903 A | 5/2013 |
| WO | 8404390 A1 | 11/1984 |
| WO | WO2015/034513 A1 | 3/2015 |
| WO | 2015/189593 A1 | 12/2015 |
| WO | 2015189593 A1 | 12/2015 |

OTHER PUBLICATIONS

John David Weickert et al., filed Dec. 12, 2016, U.S. Appl. No. 15/375,882.

John David Weickert et al., filed Jan. 27, 2016, U.S. Appl. No. 15/007,289.

U.S. Notice of Allowance issued in connection with Related U.S. Appl. No. 15/375,882 dated Feb. 1, 2017.

European Search Report and Opinion issued in connection with corresponding EP Application No. 7150893.0 dated Jun. 29, 2017.

Extended European Search Report and Opinion issued in connection with corresponding EP Application No. 17150893.0 dated Jun. 29, 2017.

* cited by examiner

ELECTROSTATIC SENSOR

FIELD OF THE INVENTION

The present subject matter relates generally to dust sensors, and more particularly, to electrostatic dust sensors for engines, such as gas turbine engines.

BACKGROUND OF THE INVENTION

A gas turbine engine generally includes, in serial flow order, a compressor section, a combustion section, a turbine section and an exhaust section. In operation, air enters an inlet of the compressor section where one or more axial or centrifugal compressors progressively compress the air until it reaches the combustion section. Fuel is mixed with the compressed air and burned within the combustion section to provide combustion gases. The combustion gases are routed from the combustion section through a hot gas path defined within the turbine section and then exhausted from the turbine section via the exhaust section.

In particular configurations, the turbine section includes, in serial flow order, a high pressure (HP) turbine and a low pressure (LP) turbine. The HP turbine and the LP turbine each include various rotatable turbine components such as turbine rotor blades, rotor disks and retainers, and various stationary turbine components such as stator vanes or nozzles, turbine shrouds, and engine frames. The rotatable and stationary turbine components at least partially define the hot gas path through the turbine section. As the combustion gases flow through the hot gas path, thermal energy is transferred from the combustion gases to the rotatable and stationary turbine components.

Such gas turbine engines are commonly employed in an aircraft. During operation of the aircraft, the engine environmental particulate and dust ingestion level is a key input to the analytics process, resulting in specific engine-by-engine action. Current dust/particulate level data is provided by ground-based and remote sensing systems. Such data has temporal and special variations as well as error, thereby making accurate assessment of engine conditions at takeoff and climb of the aircraft particularly difficult. On the other hand, if sensors are mounted on the engine, the electronics of such sensor systems are typically connected to the individual sensors via a plurality of cables and connectors. Thus, any motion or vibration of the cabling can produce more signal than the dust particles passing the sensor face, thereby resulting in a poor signal-to-noise ratio. Further, conventional engine-mounted systems can experience issues due to the triboelectric and piezoelectric effects of the cables and connectors.

Accordingly, the present disclosure is directed to an improved sensor system that addresses the aforementioned issues. More specifically, the present disclosure is directed to a sensor system that includes one or more improved electrostatic sensors having integrated electronics that more accurately detects dust particles and/or particulates within an engine, such as the gas turbine engine described above.

BRIEF DESCRIPTION OF THE INVENTION

Aspects and advantages of the invention will be set forth in part in the following description, or may be obvious from the description, or may be learned through practice of the invention.

In one aspect, the present disclosure is directed to an integrated electrostatic sensor for detecting dust in an engine, e.g. in an aircraft engine. The sensor includes an outer housing having a sensing face, an electrode configured within the outer housing adjacent to the sensing face, and an amplifier configured with the electrode. The electrode contains a plurality of electrons configured to move as charged dust particles within the engine flow past the sensing face. Thus, the amplifier is configured to detect a dust level of the engine as a function of the electron movement. The electrostatic sensor also includes a circuit board configured within the outer housing and electrically coupled to the amplifier. Thus, the circuit board is configured to send the one or more signals to a controller of the engine indicative of the dust level.

In another aspect, the present disclosure is directed to an electrostatic sensor system for an engine. The sensor system includes one or more integrated electrostatic sensors for detecting dust in the engine. Each of the electrostatic sensors includes an outer housing having sensing face, an electrode configured within the outer housing adjacent to the sensing face, and an amplifier configured with the electrode. The electrode contains a plurality of electrons configured to move as charged dust particles flow past the sensing face. Thus, the amplifier is configured to detect a dust level as a function of the electron movement. Each of the sensors also includes a circuit board configured within the outer housing and electrically coupled to the amplifier. Thus, the sensor system also includes a controller electrically coupled to the circuit board so as to receive the one or more dust signals therefrom. It should be understood that the sensor system may be further configured with any of the additional features as described herein.

In yet another aspect, the present disclosure is directed to a method for detecting dust in an engine, e.g. in an aircraft engine. The method includes providing an integrated electrostatic sensor in one or more locations of the engine, with each of the electrostatic sensors having an outer housing with a sensing face and an internal electrode and amplifier within the outer housing. Further, the electrode is adjacent to the sensing face and includes a plurality of electrons configured to move as charged dust particles flow past the sensing face. The method also includes arranging the sensing face of each sensor in a dust flow path at the one or more locations. Thus, the method also includes determining, via the amplifier of each sensor, a dust level of the engine as a function of the electron movement. Another step of the method includes generating, via a circuit board configured within the outer housing, one or more signals indicative of the dust level in response to detecting charged dust particles. It should be understood that the method may further include any additional steps and/or features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows, and "downstream" refers to the direction to which the fluid flows.

Generally, the present disclosure is directed to an electrostatic sensor system and methods for detecting dust and/or other airborne particulates in an engine, e.g. in an aircraft gas turbine engine. Further, it should be understood that the electrostatic sensor system and related methods are also suitable for any other type of engine, including but not limited to an industrial engine, a power generation engine, a land-based engine, a marine engine, or similar. More specifically, the electrostatic sensor system includes a controller electrically coupled with one or more electrostatic sensors. Further, each of the electrostatic sensors includes an outer housing having a sensing face, an electrode configured within the outer housing adjacent to the sensing face, and an amplifier configured with the electrode. The electrode contains a plurality of electrons configured to move as charged dust particles flow past the sensing face. Thus, the amplifier is configured to detect a dust level as a function of the electron movement. The electrostatic sensor also includes a circuit board configured within the outer housing and electrically coupled to the amplifier. Thus, the circuit board is configured to send the one or more signals to a controller of the engine indicative of the dust level.

Thus, the outer housing and electronics configuration minimize the distance between the sensor input and the electrode, thereby increasing sensitivity of the sensor. As such, the present disclosure provides various advantages not present in the prior art. For example, the electrostatic sensors of the present disclosure provide more accurate dust detection in engines that is robust and reliable. Further, since the electronics are integrated within the sensor, the present design requires less maintenance and suffers from fewer operational issues over prior art designs. Moreover, the amplifier low leakage current facilitates DC coupling of the amplifier, which allows low frequency changes in dust levels to be captured. In addition, the high input impedance of the electrode improves the sensor sensitivity to small changes in charge in the sensing face. Further, the high input impedance of the electrode also improves the low frequency response of the sensor by preventing the charge redistribution within the electrode caused by the sensed particles from leaking away such that an output signal cannot be produced. Thus, the electrostatic sensor of the present disclosure is capable of detecting from about one (1) part in seven (7) million by mass of dust particles. Moreover, electrostatic sensors of the present disclosure can provide ice detection, as well as volcanic ash and/or other damaging ingested particulate detection in addition to dust. In addition, the electrostatic sensor, when located in the engine exhaust nozzle, can detect internally generated particles from rubs of internal engine parts and/or deterioration of engine parts which results in the release of debris.

Figure 1:
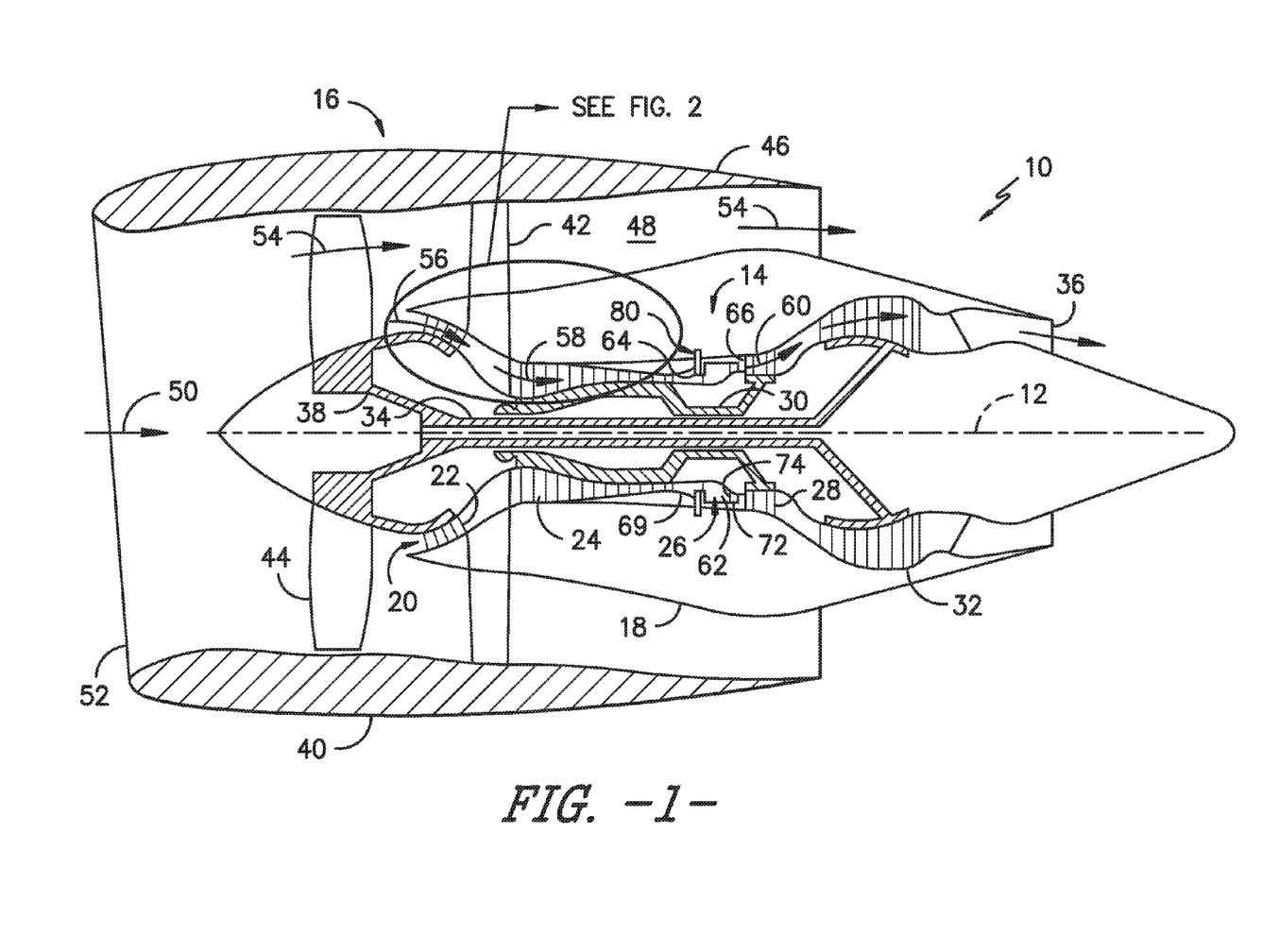
FIG. 1 illustrates a schematic cross-sectional view of one embodiment of a gas turbine engine according to the present disclosure.

Referring now to the drawings, FIG. 1 illustrates a schematic cross-sectional view of one embodiment of a gas turbine engine 10 (high-bypass type) according to the present disclosure. More specifically, the gas turbine engine 10 may include an aircraft engine. As shown, the gas turbine engine 10 has an axial longitudinal centerline axis 12 therethrough for reference purposes. Further, as shown, the gas turbine engine 10 preferably includes a core gas turbine engine generally identified by numeral 14 and a fan section 16 positioned upstream thereof. The core engine 14 typically includes a generally tubular outer casing 18 that defines an annular inlet 20. The outer casing 18 further encloses and supports a booster 22 for raising the pressure of the air that enters core engine 14 to a first pressure level. A high pressure, multi-stage, axial-flow compressor 24 receives pressurized air from the booster 22 and further increases the pressure of the air. The compressor 24 includes rotating blades and stationary vanes that have the function of directing and compressing air within the turbine engine 10. The pressurized air flows to a combustor 26, where fuel is injected into the pressurized air stream and ignited to raise the temperature and energy level of the pressurized air. The high energy combustion products flow from the combustor 26 to a first (high pressure) turbine 28 for driving the high pressure compressor 24 through a first (high pressure) drive shaft 30, and then to a second (low pressure) turbine 32 for driving the booster 22 and the fan section 16 through a second (low pressure) drive shaft 34 that is coaxial with the first drive shaft 30. After driving each of the turbines 28 and 32, the combustion products leave the core engine 14 through an exhaust nozzle 36 to provide at least a portion of the jet propulsive thrust of the engine 10.

The fan section 16 includes a rotatable, axial-flow fan rotor 38 that is surrounded by an annular fan casing 40. It will be appreciated that fan casing 40 is supported from the core engine 14 by a plurality of substantially radially-extending, circumferentially-spaced outlet guide vanes 42. In this way, the fan casing 40 encloses the fan rotor 38 and the fan rotor blades 44. The downstream section 46 of the fan casing 40 extends over an outer portion of the core engine 14 to define a secondary, or bypass, airflow conduit 48 that provides additional jet propulsive thrust.

From a flow standpoint, it will be appreciated that an initial airflow, represented by arrow 50, enters the gas turbine engine 10 through an inlet 52 to the fan casing 40. The airflow passes through the fan blades 44 and splits into a first air flow (represented by arrow 54) that moves through the conduit 48 and a second air flow (represented by arrow 56) which enters the booster 22.

The pressure of the second compressed airflow 56 is increased and enters the high pressure compressor 24, as represented by arrow 58. After mixing with fuel and being combusted in the combustor 26, the combustion products 60 exit the combustor 26 and flow through the first turbine 28. The combustion products 60 then flow through the second turbine 32 and exit the exhaust nozzle 36 to provide at least a portion of the thrust for the gas turbine engine 10.

Still referring to FIG. 1, the combustor 26 includes an annular combustion chamber 62 that is coaxial with the longitudinal centerline axis 12, as well as an inlet 64 and an outlet 66. As noted above, the combustor 26 receives an annular stream of pressurized air from a high pressure compressor discharge outlet 69. A portion of this compressor discharge air flows into a mixer (not shown). Fuel is injected from a fuel nozzle 80 to mix with the air and form a fuel-air mixture that is provided to the combustion chamber 62 for combustion. Ignition of the fuel-air mixture is accomplished by a suitable igniter, and the resulting combustion gases 60 flow in an axial direction toward and into an annular, first stage turbine nozzle 72. The nozzle 72 is defined by an annular flow channel that includes a plurality of radially-extending, circumferentially-spaced nozzle vanes 74 that turn the gases so that they flow angularly and impinge upon the first stage turbine blades of the first turbine 28. As shown in FIG. 1, the first turbine 28 preferably rotates the high-pressure compressor 24 via the first drive shaft 30, whereas the low-pressure turbine 32 preferably drives the booster 22 and the fan rotor 38 via the second drive shaft 34.

The combustion chamber 62 is housed within the engine outer casing 18 and fuel is supplied into the combustion chamber 62 by one or more fuel nozzles 80. More specifically, liquid fuel is transported through one or more passageways or conduits within a stem of the fuel nozzle 80.

Figure 2:
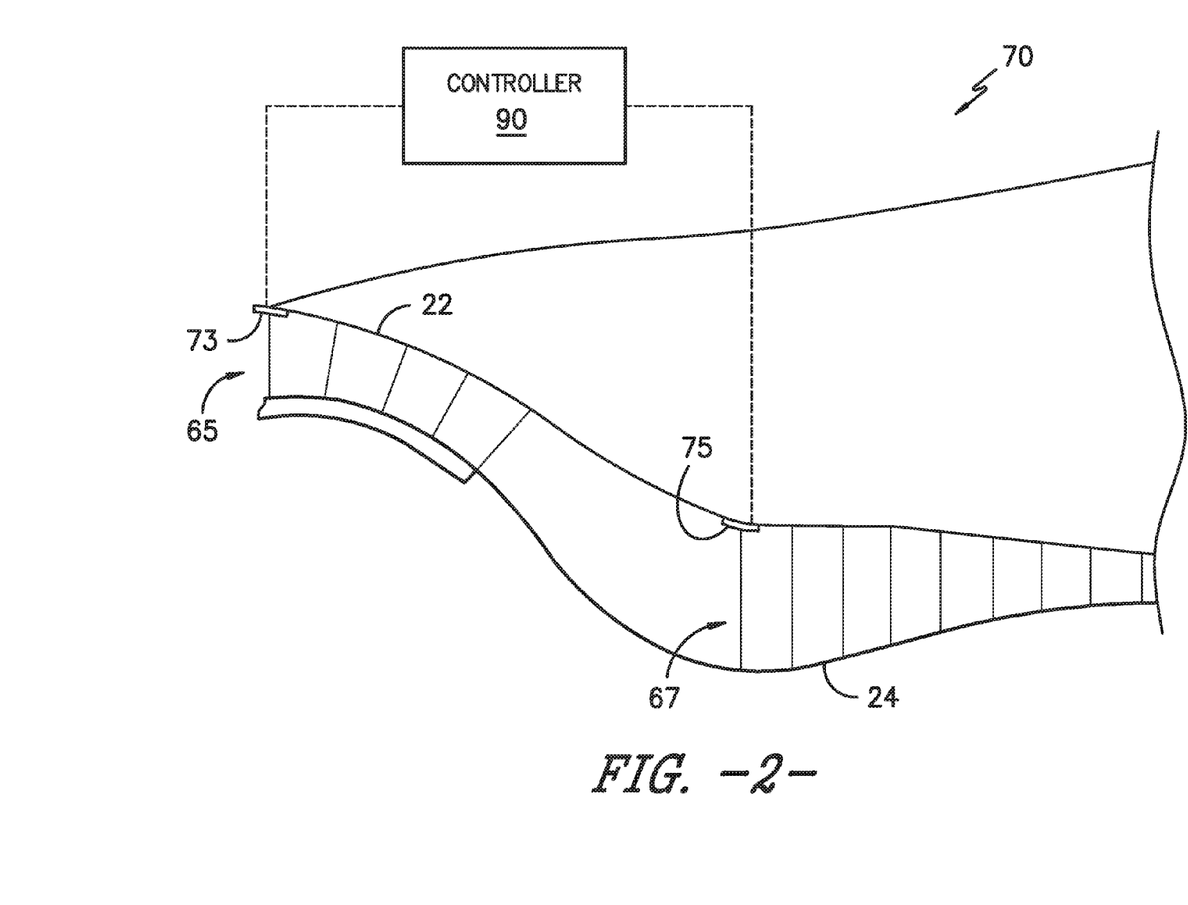
FIG. 2 illustrates a schematic diagram of one embodiment of a sensor system for detecting dust in an engine according to the present disclosure.
Figure 3:
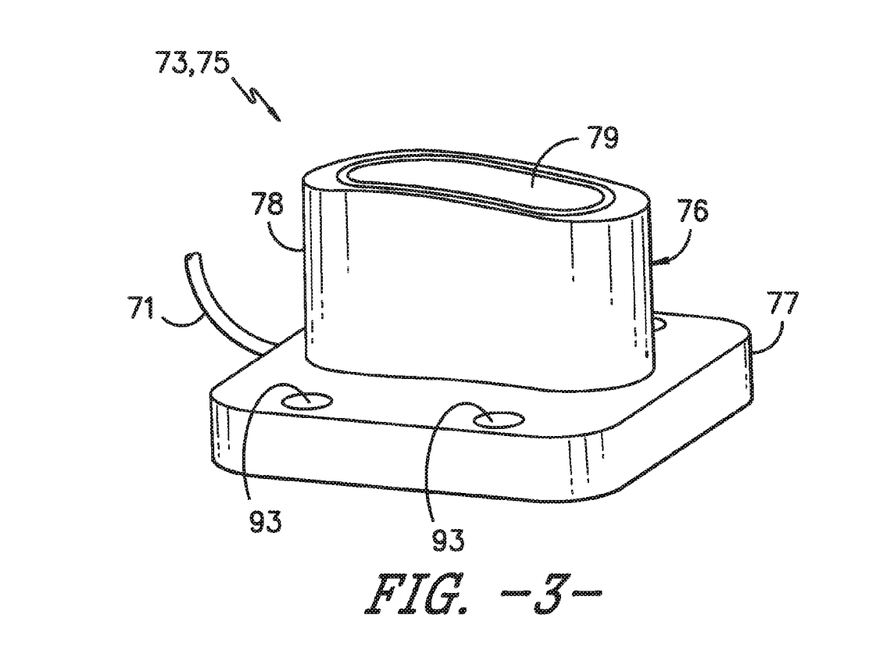
FIG. 3 illustrates a perspective view of one embodiment of an electrostatic sensor for detecting dust in an engine according to the present disclosure.
Figure 4:
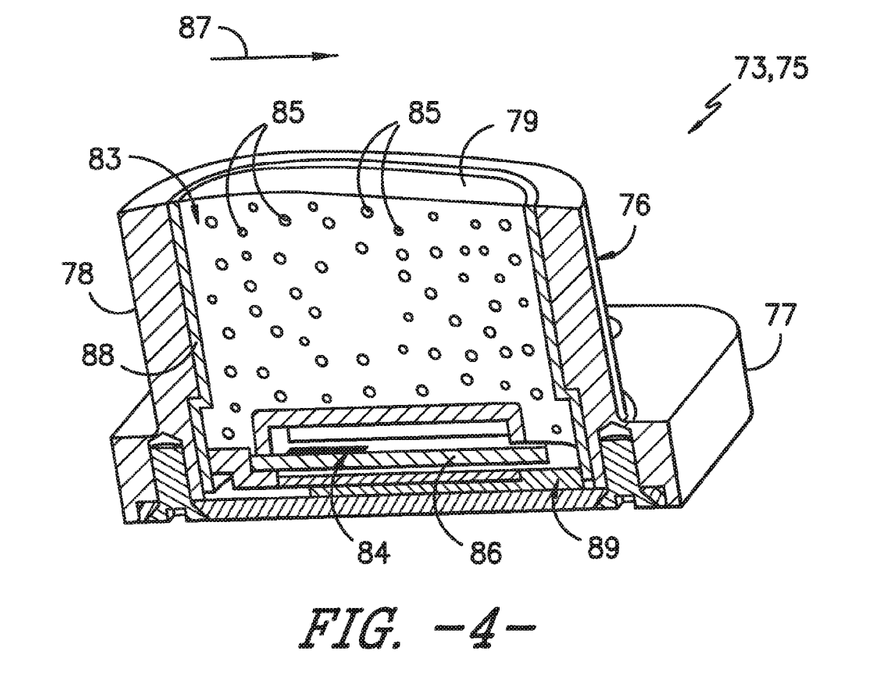
FIG. 4 illustrates a cross-sectional view of one embodiment of an electrostatic sensor for detecting dust in an engine according to the present disclosure.
Figure 5:
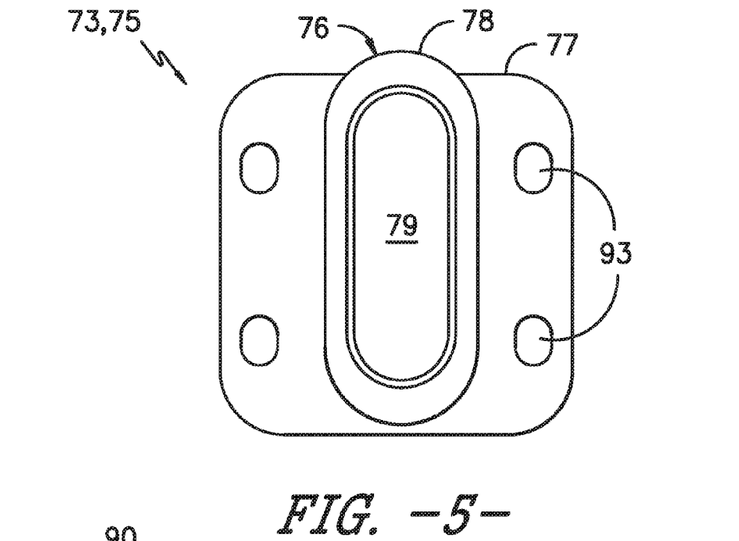
FIG. 5 illustrates a top view of one embodiment of an electrostatic sensor for detecting dust in an engine according to the present disclosure.

During operation, dust and other types of aerosol particulates are ingested by the gas turbine engine 10, e.g. from air entering the inlet 52. Dust and aerosol particulate accumulation is a key input for engine analytics as these levels are important in evaluating engine service time, wear and tear, and/or other maintenance schedules. Thus, the present disclosure is directed to an improved electrostatic sensor system 70 (FIG. 2) and method 100 (FIG. 7) for detecting dust in the gas turbine engine 10, e.g. in an aircraft engine. More specifically, as shown in FIG. 2, the sensor system 70 includes one or more electrostatic sensors 73, 75 communicatively coupled to a controller 90. In addition, as shown in FIGS. 3-5, various views of an electrostatic sensor (e.g. sensors 73 and 75) are illustrated. For example, FIG. 3 illustrates a perspective view of one of the electrostatic sensors 73, 75 with associated sensor power/output wiring 71; FIG. 4 illustrates a cross-sectional view of one of the electrostatic sensors 73, 75; and FIG. 5 illustrates a top view of one of the electrostatic sensors 73, 75.

As shown, each of the electrostatic sensors 73, 75 defines an outer housing 76 or casing that includes a sensing face 79. More specifically, the outer housing 76 includes a base or mounting portion 77 and a sensing portion 78. Thus, the mounting portion 77 is configured to be mounted or secured to the gas turbine engine 10, whereas the sensing portion 78 is configured to detect dust particles in the engine 10 via the sensing face 79. More specifically, as shown particularly in FIG. 4, the sensing portion 78 defines a profile having a predetermined shape with the sensing face 79 configured to be arranged in an area of the engine 10 prone to dust being entrained with the airflow. It should be understood that the sensing portion 78 of the outer housing 76 may have any suitable shape. For example, in certain embodiments, the sensing portion 78 of the housing 76 may have a predetermined shape configured to fit in an existing location, a hole, or inlet of the gas turbine engine 10 such that the sensing face 79 is flush with an internal surface of the gas turbine engine 10. More specifically, as shown, the sensing portion 78 may have a generally oblong or oval shape. Such a shape generally corresponds to an existing inlet location of the engine 10, such as but not limited to a compressor inlet 67 (FIG. 2), a booster inlet 65 (FIG. 2), a turbine inlet, a borescope inlet, or any other suitable inlet or location of the engine 10 that experiences dust exposure.

Referring particularly to FIG. 4, the electrostatic sensors 73, 75 also include an internal electrode 83 and amplifier 84 configured within the sensing portion 78 of the outer housing 76, i.e. adjacent to the sensing face 79. For example, as shown in the illustrated embodiment, the electrode 83 includes a plurality of electrons 85 configured adjacent to the sensing face 79. Thus, as indicated by arrow 87, the electrons 85 are configured to move or flow as charged dust particles flow past the sensing face 79. More specifically, the electrons 85 move within the electrode 83 either towards or away from the sensing faces 79 based on the charge of the passing dust particles. Accordingly, the amplifier 84 is configured to detect or measure the location of the electrons 85 within the electrode so as to indicate a dust level of the charged dust particles flowing past the sensing face 79.

As mentioned, the integrated amplifier 84 of the present disclosure is extremely sensitive and capable of more accurately detecting dust levels of the engine 10. More specifically, in certain embodiments, the amplifier 84 may include a leakage current of from about 1 femtoampere to about 5 femtoamperes, more preferably about 3 femtoamperes. Thus, the low leakage current facilitates DC coupling of the amplifier 84, which allows low frequency changes in dust levels to be captured. Further, the electrode 83 may have an impedance of greater than about 1 G-Ohm, for example about 10 G-Ohm. As such, the high input impedance of the electrode 83 is configured to improve the sensor sensitivity to small changes in charge in the sensing face 79. Further, the high input impedance is also configured to improve the low frequency response of the sensor 73, 75 by preventing sensed charge from leaking away such that an output voltage cannot be produced. Moreover, the amplifier 84 may have an operating temperature range of from about 100 degrees Celsius (° C.) to about 250° C., more preferably from about 150° C. to about 230° C. Thus, the electrostatic sensor(s) 73, 75 of the present disclosure is capable of detecting from about one (1) part in seven (7) million by mass of dust particles.

In additional embodiments, the electrostatic sensor(s) 73, 75 is further configured to detect any/all airborne aerosol particulates including but not limited to ice crystals, construction debris, sand, and/or volcanic ash within the engine flowpath and alert the controller 90 in the event of such detection. Further, the electrostatic sensor(s) 73, 75 is further configured to detect internally-generated dust and debris and alert the controller.

Referring particularly to FIG. 4, the electrostatic sensors 73, 75 also include an integrated circuit board 86 configured within the outer housing 76 and electrically coupled to the amplifier 84. More specifically, as shown, the circuit board 86 may be configured adjacent to the electrode 83 and opposite the sensing face 79. In additional embodiments, the circuit board 86 may be located at any suitable location within the outer housing 76 of the sensor 73, 75. Further, the circuit board 86 as described herein may include any suitable circuit board that mechanically supports and electrically connects the electronic components within the outer housing 76 of the sensor(s) 73, 75. More specifically, certain circuit boards of the present disclosure may include conductive tracks, pads, and/or other features etched from metal, such as copper, sheets that are laminated onto a non-conductive substrate. Further, the circuit board 86 of the present disclosure may be single-sided, double-sided, or multi-layered. Thus, the circuit board 86 as described herein is configured to send one or more signals to the controller 90 of the engine 10 that are indicative of the dust level.

As shown in FIG. 4, the electrostatic sensor(s) 73, 75 may also include one or more insulators or insulation layers 88, 89. For example, as shown in FIG. 4, the electrostatic sensor(s) 73, 75 may include one or more insulation layers 88 between the electrode 83 and the outer housing 76. In addition, the electrostatic sensor(s) 73, 75 may include one or more insulation layers 89 between the mounting portion 77 of the outer housing 76 and the engine 10. It should further be understood that any number of insulation layers may be employed at any suitable location within the sensor 73, 75.

In addition, as shown in FIGS. 3 and 5, the mounting portion 77 of the sensor 73, 75 may include one or more through holes 93 configured for mounting the electrostatic sensor(s) 73, 75 at any suitable location of the engine 10. More specifically, in certain embodiments, each of the through holes 93 may be configured to receive a fastener (e.g. a threaded bolt) so as to secure the sensors 73, 75 in a desired location. Alternatively, the electrostatic sensor(s) 73, 75 may be secured or mounted within the engine 10 via any other suitable methods, including but not limited to metal clips, welded nichrome foil, or similar.

Figure 6:
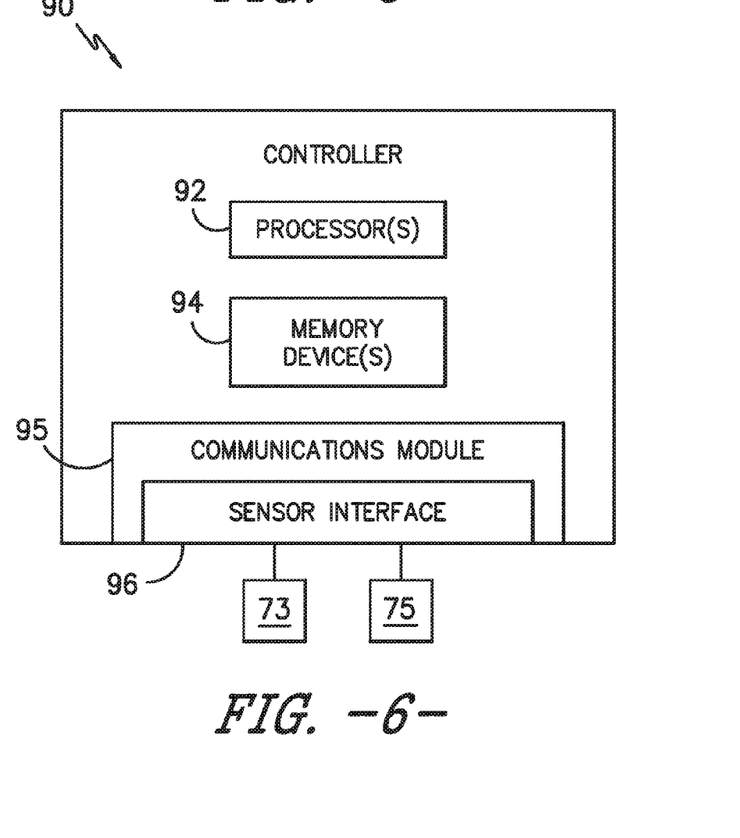
FIG. 6 illustrates a block diagram of one embodiment of suitable components that may be included in a controller of an engine according to the present disclosure.

Referring now to FIGS. 2 and 6, the controller 90 is configured to receive the dust signals from the sensors 73, 75. More specifically, as shown in FIG. 6, there is illustrated a block diagram of one embodiment of suitable components that may be included in the controller 90 according to the present disclosure. As shown, the controller 90 may include one or more processor(s) 92 and associated memory device(s) 94 configured to perform a variety of computer-implemented functions (e.g., performing the methods, steps, calculations and the like and storing relevant data as disclosed herein). Additionally, the controller 90 may also include a communications module 95 to facilitate communications between the controller 90 and the electrostatic sensor(s) 73, 75. Further, the communications module 95 may include a sensor interface 96 (e.g., one or more analog-to-digital converters) to permit signals transmitted from the sensor(s) 73, 75 to be converted into signals that can be understood and processed by the processor(s) 92. It should be appreciated that the sensor(s) 73, 75 may be communicatively coupled to the communications module 95 using any suitable means. For example, as shown in FIG. 6, the sensors 73, 75 are coupled to the sensor interface 96 via a wired connection. However, in other embodiments, the sensors 73, 75 may be coupled to the sensor interface 96 via a wireless connection, such as by using any suitable wireless communications protocol known in the art. As such, the processor(s) 92 may be configured to receive one or more signals from the sensors 73, 75.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 92 may generally include memory element(s) including, but not limited to, computer readable medium (e.g., random access memory (RAM)), computer readable non-volatile medium (e.g., a flash memory), cloud storage, a floppy disk, a compact disc-read only memory (CD-ROM), a magneto-optical disk (MOD), a digital versatile disc (DVD) and/or other suitable memory elements. Such memory device(s) 94 may generally be configured to store suitable computer-readable instructions that, when implemented by the processor(s) 92, configure the controller 90 to perform various functions of the gas turbine engine 10.

Figure 7:
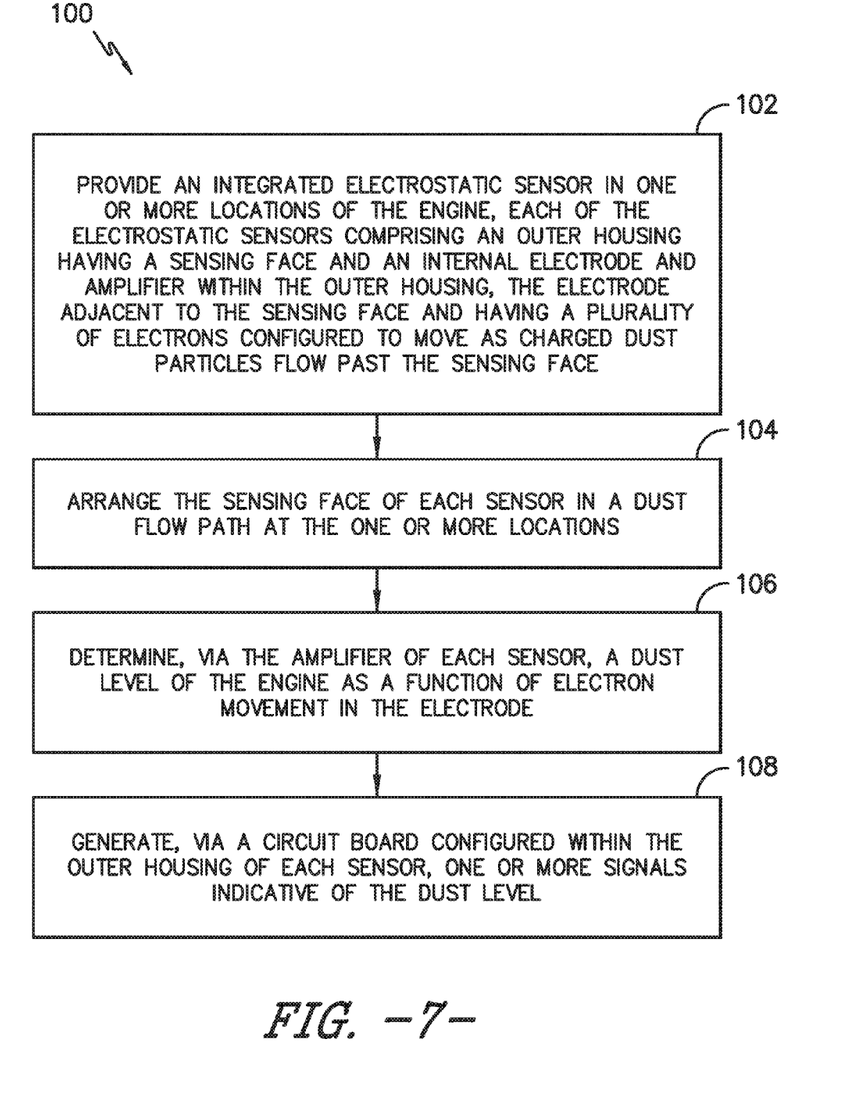
FIG. 7 illustrates a flow diagram of one embodiment of method for detecting dust in an engine according to the present disclosure.

Referring now to FIG. 7, a flow diagram of one embodiment of a method 100 for detecting dust in a gas turbine engine 10, e.g. an aircraft engine, is illustrated. As shown at 102, the method 100 includes providing an integrated electrostatic sensor (e.g. sensors 73, 75) in one or more locations in the gas turbine engine 10, with each of the electrostatic sensors 73, 75 having an outer housing 76 with a sensing face 79 and an internal electrode 83 and amplifier 84 within the outer housing 76. Further, as mentioned, the electrode 83 is adjacent to the sensing face 79 and contains a plurality of electrons 85 configured to move as charged dust particles flow past the sensing face 79. As shown at 104, the method 100 includes arranging the sensing face 79 of each sensor 73, 75 in a dust flow path at the one or more locations. Thus, as shown at 106, the method 100 also includes determining, via the amplifier 84 of each sensor 73, 75, a dust level of the gas turbine engine 10 as a function of the electron movement. As shown at 108, the method 100 includes generating, via a circuit board 86 configured within the outer housing 76, one or more signals indicative of the dust level in response to detecting charged dust particles.

In one embodiment, the method 100 may also include sending, via the circuit board 86 of the each of the electrostatic sensors 73, 75, the signal(s) to the controller 90 of the gas turbine engine 10. As such, the sensors 73, 75 described herein provide real-time, accurate particulate level data to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An integrated electrostatic sensor for detecting charged dust particles, the sensor comprising:

an outer housing;

an electrode configured within the outer housing, wherein the electrode comprises an impedance of greater than about 1 G-Ohm, the electrode further comprising a first end and a second end separated by a predetermined length, the second end comprising a sensing face that is substantially flush with an edge of the outer housing, configured such that electrons within the electrode move as charged dust particles flow past the sending face;

an amplifier configured within the outer housing and electrically coupled to the electrode, wherein the amplifier comprises a leakage current of from about 1 femtoampere to about 5 femtoampere, the amplifier configured to detect a dust level as a function of the electron movement; and a circuit board configured within the outer housing and electrically coupled to the amplifier, the circuit board configured to generate one or more signals indicative of the dust level.

2. The sensor of claim 1, wherein the amplifier comprises an operating temperature range of from about 100 degrees Celsius to about 250 degrees Celsius.

3. The sensor of claim 1, wherein the circuit board is configured adjacent to the electrode in a position that is opposite from the sensing face of the outer housing.

4. The sensor of claim 1, wherein the electrostatic sensor is further configured to detect at least one of ice crystals, construction debris, sand, volcanic ash, or charged airborne particulates.

5. The sensor of claim 1, wherein the electrostatic sensor is further configured to detect internally-generated dust and debris of an engine and alert a controller of the engine.

6. The sensor of claim 1, wherein the outer housing comprises a sensing portion comprising the sensing face and a mounting portion configured for securing the sensor in a mounting location.

7. The sensor of claim 6, wherein the sensing portion of the outer housing comprises a generally oblong shape.

8. The sensor of claim 6, wherein the mounting portion comprises a generally rectangular shape.

9. The sensor of claim 6, further comprising one or more insulators configured between at least one of (1) the electrode and the outer housing or (2) the mounting portion and the mounting location.

10. The sensor of claim 6, wherein the mounting portion comprises one or more through holes configured for mounting the sensor to the mounting location.

11. The sensor of claim 6, wherein the sensing portion of the outer housing comprises a predetermined shape configured to fit in an existing location of an engine such that the sensing face is flush with an internal surface of the engine.

12. The sensor of claim 11, wherein the existing location comprises at least one of a borescope inlet, a compressor inlet, a booster inlet, or a turbine inlet of the engine.

13. An electrostatic sensor system, the sensor system comprising:

one or more integrated electrostatic sensors for detecting charged dust particles, each of the electrostatic sensors comprising:

an outer housing, an electrode configured within the outer housing, wherein the electrode comprises an impedance of greater than 1 G-Ohm, the electrode comprising a first end and a second end separated by a predetermined length, the second end comprising a sensing face that is substantially flush with the edge of the outer housing, configured such that a plurality of electrons configured to move as charged dust particles flow past the sensing face, wherein the amplifier has an operating temperature range of from about 100 degrees Celsius to about 250 degrees Celsius;

an amplifier configured within the outer housing and electrically coupled to the electrode, wherein the amplifier comprises a leakage current of from about 1 femtoampere to 5 femtoamperes, the amplifier configured to detect a dust level as a function of the electron movement, and a circuit board configured within the outer housing and electrically coupled to the amplifier, the circuit board configured to generate signals indicative of the dust level; and a controller electrically coupled to the circuit board so as to receive the one or more signals therefrom.

14. The system of claim 13, wherein the outer housing comprises a sensing portion comprising the sensing face and a mounting portion configured for securing the sensor in a mounting location.

15. The system of claim 14, further comprising one or more insulators configured between at least one of (1) the electrode and the outer housing or (2) the mounting portion and the mounting location.

* * * * *